United States Patent
Husmark et al.

(10) Patent No.: US 9,962,324 B2
(45) Date of Patent: May 8, 2018

(54) COMPOSITION COMPRISING A BUFFERED LACTIC ACID

(71) Applicant: SCA Hygiene Products AB, Göteborg (SE)

(72) Inventors: Ulrika Husmark, Göteborg (SE); Ulla Forsgren Brusk, Göteborg (SE); Chatrine Stridfeldt, Göteborg (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 0 days. days.

(21) Appl. No.: 14/892,058

(22) PCT Filed: May 30, 2013

(86) PCT No.: PCT/SE2013/050622
§ 371 (c)(1),
(2) Date: Nov. 18, 2015

(87) PCT Pub. No.: WO2014/193279
PCT Pub. Date: Dec. 4, 2014

(65) Prior Publication Data
US 2016/0128921 A1    May 12, 2016

(51) Int. Cl.
*A61K 8/36* (2006.01)
*A61K 8/365* (2006.01)
(Continued)

(52) U.S. Cl.
CPC .......... *A61K 8/365* (2013.01); *A61F 13/8405* (2013.01); *A61K 31/19* (2013.01);
(Continued)

(58) Field of Classification Search
CPC .......... A61K 8/00; A61K 8/02; A61K 8/0204; A61K 8/0216; A61K 8/04; A61K 8/042;
(Continued)

(56) References Cited

U.S. PATENT DOCUMENTS 5,201,326 A    4/1993    Kubicki et al.
6,359,191 B1   3/2002    Rusch et al.
(Continued)

FOREIGN PATENT DOCUMENTS

CN    101678147 A    3/2010
DE    103 29 361 A1   1/2005
(Continued)

OTHER PUBLICATIONS

L. L Melvin et al (pH-balanced tampons: do they effectively control vaginal pH?, BJOG DOI: 10:1111/j.1471-0528.2008.01666.x hereafter Melvin).*
(Continued)

*Primary Examiner* — Micah Paul Young
(74) *Attorney, Agent, or Firm* — Drinker Biddle & Reath LLP

(57) ABSTRACT

A composition including a buffered lactic acid having a pH within the range of from 3.0 to 6.5 is disclosed. The composition is a lubricant composition and has a water activity of from 0.03 to 0.60. The friction between the absorbent product and the skin/mucous membrane of the user is reduced when in contact with the skin or mucous membrane of the user. An additional advantage is that the composition has a pH in the acidic range which is close to the pH of the skin and/or mucous membrane.

17 Claims, 10 Drawing Sheets

(51) Int. Cl.
*A61K 31/19* (2006.01)
*A61L 15/20* (2006.01)
*A61L 15/50* (2006.01)
*A61F 13/84* (2006.01)
*A61Q 17/00* (2006.01)

(52) U.S. Cl.
CPC ............... *A61L 15/20* (2013.01); *A61L 15/50* (2013.01); *A61Q 17/00* (2013.01); *A61F 2013/8411* (2013.01); *A61F 2013/8455* (2013.01)

(58) Field of Classification Search
CPC .......... A61K 8/044; A61K 8/046; A61K 8/06; A61K 8/062; A61K 8/18; A61K 8/19; A61K 8/67
USPC ................................................ 424/400–468
See application file for complete search history.

(56) References Cited

U.S. PATENT DOCUMENTS

| | | | |
|---|---|---|---|
| 6,610,741 B1* | 8/2003 | Mukherjee | ............... A61K 8/04 514/557 |
| 2003/0143262 A1* | 7/2003 | Brusk | .................. A61K 8/0208 424/443 |
| 2004/0167039 A1 | 8/2004 | Ahmad et al. | |
| 2004/0241151 A1 | 12/2004 | Husmark et al. | |
| 2006/0122569 A1 | 6/2006 | Drevik et al. | |
| 2009/0156979 A1 | 6/2009 | Andersch | |

FOREIGN PATENT DOCUMENTS

| | | | |
|---|---|---|---|
| EP | 2130531 | A1 | 12/2009 |
| JP | H11285513 | A | 10/1999 |
| JP | 2003012490 | A | 1/2003 |
| JP | 2009/521255 | A | 6/2009 |
| JP | 2013/519807 | A | 5/2013 |
| JP | 2013/543763 | A | 12/2013 |
| WO | WO-2004/101008 | A1 | 11/2004 |
| WO | WO-2005/035013 | A1 | 4/2005 |
| WO | WO-2007/073265 | A1 | 6/2007 |
| WO | WO-2008/156398 | A1 | 12/2008 |
| WO | WO-2011/103183 | A1 | 8/2011 |
| WO | WO-2012/065073 | A2 | 5/2012 |

OTHER PUBLICATIONS

L Melvin et al., "pH-balanced tampons: do they effectively control vaginal pH?", BJOG An International Journal of Obstetrics and Gynaecology, p. 639-p. 645, 2008.
EP Application 13885512.7—Extended European Search Report dated Dec. 22, 2016.
Decision of Rejection dated Apr. 19, 2017 in Chinese Patent Application No. 201380077057.5 (w/ partial translation).
Office Action dated Jul. 29, 2016 in Chinese Patent Application No. 201380077057.5 (6 pages) with an English Translation (5 pages).
JP Application 2016-512874—Notice of Reasons for Rejection dated Sep. 16, 2016.
Japanese Application No. 2016-512874—English translation of the Notice of Reasons for Rejection dated May 29, 2017.
Russian Application No. 2015156063—Decision to Grant dated Apr. 25, 2017 (w/ English translation).
Wikipedia page of "Water Activity" in Japanese, available at https://ja.wikipedia.org/wiki/%E6%B0%B4%E5%88%86%E6%B4%BB%E6%80%A7 (w/ machine English translation).
Office Action issued having response deadline of Sep. 8, 2017 in Columbia Patent Application No. 15306892 (4 pages) with a partial English translation (5 pages).
Office Action with Search Report dated Nov. 2, 2017 having response deadline of Feb. 5, 2018 in Columbia Patent Application No. 15306892 (10 pages) with a partial English translation (10 pages).
Swidsinski A et al., 2012, *Positive effects of local therapy with a vaginal lactic acid gel on dysuria and E.coli bacteriuria question our current views on recurrent cystitis*. Arch Gynecol Obstet. 285(6):1619-25. Epub Jan. 5, 2012.

* cited by examiner

COMPOSITION COMPRISING A BUFFERED LACTIC ACID

CROSS-REFERENCE TO PRIOR APPLICATION

This application is a § 371 National Stage Application of PCT International Application No. PCT/SE2013/050622 filed May 30, 2013, which is incorporated herein in its entirety.

TECHNICAL FIELD

The present disclosure relates to a composition including a buffered lactic acid, to a cream including the composition and to a hygiene and/or absorbent product including the composition and to a use of a buffered lactic acid as a lubricant.

BACKGROUND ART

Skin functions as a body's barrier to the environment and mucous membranes function as linings for cavities that are exposed to the external environment and internal organs. For example, urogenital areas include mucous membranes.

Absorbent products, such as tampons for intra-vaginal use and wearable absorbent products such as diapers, sanitary napkins and incontinence products have long been in use to absorb bodily fluids, such as urine and/or blood. Other hygiene products, such as wipes and/or towels have been used for example for cleaning purposes.

When the tampon is inserted into a vagina, the mucous membrane of the user may be irritated due to friction between the mucous membrane and the tampon. Further, if mucous membrane is fragile and/or dry it may be difficult and painful to use regular tampons. Also wearable absorbent products and hygiene products, such as wipes and/or towels may chafe sensitive skin during use. Consequences of the use may be damaged skin or mucous membrane with small wounds and irritations. The skin may be further damaged or irritated when for example urine or blood comes into contact with the damaged skin.

Problems with skin irritation due to friction between the skin and/or the mucous membrane of a user and absorbent and/or hygiene products may thus occur.

Accordingly, there is a need to reduce the risk for irritation in mucous membrane and/or skin irritation, especially when absorbent and/or hygiene products are used.

SUMMARY

It is desired to provide a composition which reduces the risk for irritation in mucous membrane and/or skin. It is also desired to provide a composition that protects the skin, and for example increases the resistance of the skin or mucous membrane to absorbent or hygiene products that are adapted to contain urine, blood, and/or other body liquids and that come into contact with the skin or the mucous membrane.

Disclosed is a composition including a buffered lactic acid having a pH within the range of from 3.0 to 6.5, and a water activity of from 0.03 to 0.60. It has been surprisingly found that the composition is lubricating and is thus a lubricant. The composition is gel-like, viscous and slippery, and provides these features to skin to which it is applied. The composition may be used as such, e.g. as a barrier cream, or the composition may be used together with the use of a hygiene and/or absorbent product. When the composition is used together with the use of hygiene and/or absorbent products the composition reduces friction between the user and an absorbent/hygienic product, thus enabling the use of tampons, wearable absorbent products and hygienic products, such as wipes or towels, by a user having a sensitive skin and/or dry or fragile mucous membrane.

An additional advantage is that the composition has a pH in the acidic range which is close to the pH of the skin and/or mucous membrane.

The composition may be aimed for use in a method for protecting skin and/or mucous membrane against chafing by applying to the skin and/or mucous membrane a layer of the lubricant composition. In this way, the composition functions as a barrier and when the composition is used together with an absorbent and/or hygiene product the friction between the skin and/or mucous membrane of the user and the absorbent and/or hygiene product can be reduced when the product is in contact with the skin and/or mucous membrane. When the composition is used together with an absorbent and/or hygiene product, the composition may be applied to the absorbent and/or hygiene product or it may be applied to the skin and/or mucous membrane in a separate step. An advantage with applying the composition in a separate step is that the composition may be applied to an area on the skin and/or mucous membrane where the composition is most needed that can be different for different users and circumstances.

The composition is alternatively or additionally aimed for use in a method for protecting skin and/or mucous membrane against chafing by applying to at least a portion of a hygiene and/or an absorbent product a layer of the lubricant composition, wherein the composition is brought in contact with the skin of the wearer during use. These products are thus rendered more slippery and smooth, either locally or over the entire surface of the products depending on where in the product the lubricating composition is applied. The lubricating composition may be applied on the areas of the wearable absorbent product that come into contact with the urogenital areas of the user, whereby a product with advantageous skin caring properties is provided while problems with chafing are reduced.

The composition can obtain the desired water activity by drying. Drying can be performed in controlled conditions, and thus repeatable results for the water activity can be obtained in an efficient way.

The composition may have pH within the range of from 3.5 to 5.5, which is advantageous from a skin/mucous membrane care point of view.

The water activity of the composition is from 0.03 to 0.60. For example, the water activity can be from 0.10 to 0.50 or from 0.10 to 0.30. It is advantageous to keep the water activity less than 0.50, since the amount of free water in the composition is thus low. Since there is only a very small amount of free water in the composition, microbial growth can be inhibited and the product can be kept hygienic during storage. Another advantage is that no preservative is needed.

The salt buffering the lactic acid may be an alkali metal salt of lactic acid. The salt can be for example potassium lactate.

The composition may further include an essentially water-free additive. These water-free additives may further contribute to the skin and/or mucous membrane caring properties of the composition and thus improve the properties of the absorbent product. Since the additive is substantially water-free, microbial growth can be prevented. The water-free additive may be for example hydrophobic and naturally essentially water-free additive such as oils, waxes and fats. The addition of these hydrophobic substances can increase the barrier properties of the formulation and hence improve the protection of skin against irritating substances. Examples of oils are vegetable and mineral oils. Examples of waxes are petrolatum, beeswax, silicone wax, vegetable waxes. Examples of fats are lanolin and cocoa butter.

Additives can also be dried to be essentially water free. Examples of additives that can be dried and may contribute to soothing and/or prevention of infection/irritation are: botanical actives, prebiotic substances, probiotic bacteria, minerals, inorganic additives, salts and vitamins. The additive used in the composition may be chosen from these additives.

The amount of the buffered lactic acid in the composition may be from 10 to 100 weight-%, based on the total weight of the composition. Within this range, besides having very good lubricating properties, the composition has also preferable pH regulating properties.

Further disclosed is a hygiene product including the composition defined above.

Also disclosed is an absorbent product including the composition defined above. The composition may be located on or in a surface layer of the absorbent product, which layer faces the user during use. In this way, the composition can come into contact with the skin or mucous membrane of the user, and thus friction between the product and the skin and/or mucous membrane can be decreased.

Also disclosed is a use of a buffered lactic acid as a lubricant, wherein the lubricant has a pH within the range of from 3.0 to 6.5 and a water activity of from 0.03 to 0.60. The buffered lactic acid may be dried to obtain the desired water activity.

Other features and advantages of the invention are described below also with reference to the appended drawings.

DETAILED DESCRIPTION OF PARTICULAR EMBODIMENTS

By "absorbent product" is meant a product that absorbs or is adapted to absorb bodily fluids, such as urine or blood.

By "wearable absorbent product" is meant an absorbent article which is to be worn by the user, such as a diaper, pant-type diaper, sanitary napkin, panty-liner or incontinence product.

By "hygiene product" is meant a hygiene product for personal cleaning and/or wiping. The hygiene product may include tissue and/or nonwoven. Examples of hygiene products are a wet wipes, dry wipes, washcloths, patches, towelettes, napkins, handkerchiefs, personal cleansing such as make-up wipes and the like. The hygiene product is mainly aimed for wiping or cleaning purposes.

By "buffered" is meant that a salt of weak acid (or base) has been added to a composition to resist changes in its acidity (or alkalinity) and thus the pH of the composition has been stabilized.

"Water activity" of a composition is defined as the ratio of the vapor-pressure of water in the composition (p) to the vapor-pressure of pure water ($p_0$) at the same temperature. Hence water activity of pure water $a_w$=1, 0. Water activity can also be expressed as "free" or "available" water in the composition. Water activity affects physical properties of the composition as well as rates of deteriorative reactions and microbial growth during storage.

By "lubricating" or "lubricant" is meant a substance or composition that serves to lubricate, thus making a surface onto which the composition is applied slippery.

The absorbent product may be for example a tampon, diaper, sanitary napkin or incontinence product and includes a lubricating composition.

In accordance with an embodiment of the present invention, the lubricating composition includes a buffered lactic acid having a pH within the range of from 3.0 to 6.5, and a water activity of less than or equal with 0.60, e.g. from 0.03 to 0.60. It has been surprisingly found out that the composition is gel-like and slippery in consistency, and thus provides for a lubricating effect when used in absorbent products. The composition is also slightly acidic and thus suitable for use in close contact with the skin and/or mucus membrane of a wearer of the absorbent product. Further, since the composition is dried to a low water activity, there is no or a very small risk for microbial growth in the composition, and hence no preservative is needed. Therefore, the composition has been found to be suitable for use in absorbent products. The amount of buffered lactic acid may be of from 10 to 100 weight-%.

The pH of the composition may be within the range of from 3.5 to 5.5, since the human skin and mucous membrane are slightly acidic. Thus risk of skin irritation can be reduced. The pH of the composition may be modified or adjusted by varying the ratio of the buffering salt and lactic acid in the composition. The buffering salt may be for example an alkaline earth metal salt or alkali metal salt of lactic acid. Also alkali solutions such as potassium hydroxide may be used to buffer lactic acid.

The water activity of the composition is from 0.03 to 0.60 and may be obtained by drying the composition to a desired water activity. The water activity may be from 0.10 to 0.50, such as from 0.10 to 0.30, whereby there is a very low or practically no microbial proliferation in the composition.

The composition may include an essentially water-free additive. As mentioned above, the water-free additive may be for example hydrophobic and naturally essentially water-free additive such as oils, waxes and fats. The addition of these hydrophobic substances can increase the barrier properties of the formulation and hence improve the protection of skin against irritating substances. Examples of oils are vegetable and mineral oils. Examples of waxes are petrolatum, beeswax, silicone wax, vegetable waxes. Examples of fats are lanolin and cocoa butter.

Additives can also be dried to be essentially water free. Examples of additives that can be dried and may contribute to soothing and/or prevention of infection/irritation are: botanical actives, prebiotic substances, probiotic bacteria, minerals, inorganic additives, salts and vitamins. The additives further improve the properties of the composition making the composition smooth and providing skin and/or mucous membrane caring properties to the composition. The additive can be added to the composition after the buffered lactic acid has been dried to a desired water activity. If the additive needs to be dried, it may be added to the composition prior to drying and be dried as a mixture. The amount of the water free additive may be of from 0 to 90% by weight, based on the total dry weight of the composition, for example, the amount is of from 0 to 40% by weight, based on the total weight of the composition.

According to embodiments of the invention, hygiene and/or absorbent products include the above-defined composition. The composition can be added on at least a portion of the product so as to be transferable to the skin of the user during use. The composition is thus used in a method for protecting skin and/or mucous membrane against chafing by applying to at least a portion of the product a layer of the lubricant composition, which is then transferred to the skin of the wearer during use.

According to embodiments of the present invention, the composition includes the buffered lactic acid may be coated on the surface of the hygiene and/or absorbent product, e.g. on a top sheet, which faces the user, of a wearable absorbent product. The composition may be coated on the product such that the composition is located on or in a surface layer of the absorbent product. The whole surface or the product may be coated with the composition or just a portion of the product may be coated with the composition. The coating may be performed for example by immersing the product, e.g. a wipe, in the composition. The composition may be added to one or several of the mentioned positions. The composition may be applied by means of any suitable application method, such as for example spraying, coating, and/or printing. The composition may be applied to the hygiene/absorbent article in an amount ranging from 1-100 g/m$^2$.

The absorbent product may have several parts that come in to contact with the skin or mucous membrane in the urogenital area of the user. During use, chafing can be caused in the areas where the absorbent product is in contact with the skin, such as in the areas around the waist, hips, and legs, or in case of a tampon, in the mucous membrane of the vagina. Chafing can also be caused in the urogenital areas of the user that is in the crotch area or the wearable product. These areas are also wet areas of the absorbent products, i.e. areas where the absorbent product receives and stores urine and/or blood. The composition of embodiments of the present invention protects the skin against chafing.

According to embodiments of the present invention, the wearable absorbent product may include the lubricating composition over a part of the surface of the product, e.g. on parts of the top sheet of the product or on the top surface of a tampon that is in contact with the skin and/or mucous membrane of the user. The lubricating composition may be applied on the parts of the product that come into contact with the urogenital areas of the user, e.g. in the crotch region of the wearable absorbent product. When the lubricating composition is applied to the crotch region of the absorbent product, the skin caring properties of the lubricating agent may be utilized in the sensitive urogenital areas of the user.

Alternatively, the lubricating agent may be applied in or on the parts of the absorbent product where there is a risk for chafing of the skin and thus the lubricating composition may additionally or alternatively be applied to any portion of the article that is in contact with the skin of the wearer during use. Such portions include in addition to the edge regions of the top sheet, elasticized side flaps, barrier flaps, wings, belts in a belted diaper, and/or waist portion, hip portion, outer edges of the absorbent product, outer parts of standing gathers and/or in or on the wet parts of the product.

The composition may also be applied to the skin or mucous membrane to protect them against chafing.

BRIEF DESCRIPTION OF THE DRAWINGS

Embodiments of the invention will be described in more detail, with reference to the figures that are shown on the appended drawings. In the drawings.

DETAILED DESCRIPTION OF PARTICULAR EMBODIMENTS

Figure 1:
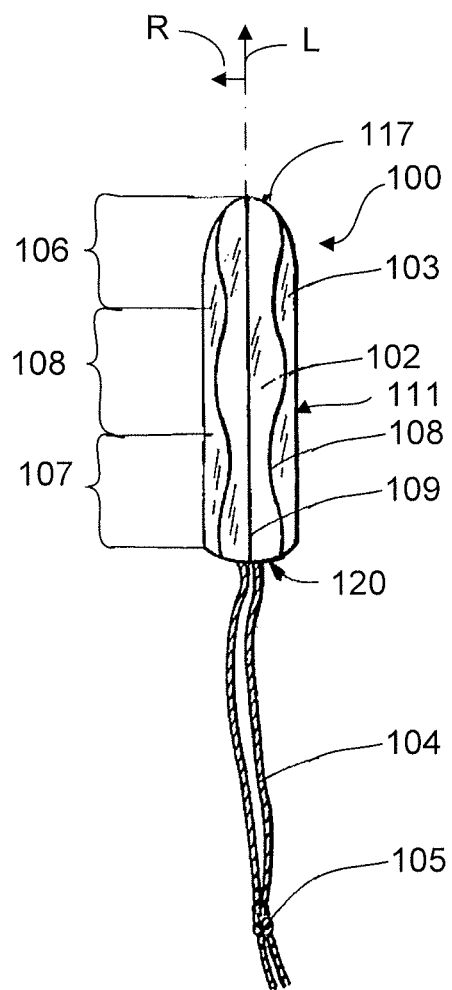
FIG. 1 shows a perspective view of a tampon including the composition according to an embodiment of the invention.

The tampon 100 shown in FIG. 1 includes an absorption body 102 enclosed in a liquid permeable cover 103 and having two withdrawal string ends 104 that are joined together in a knot 105. The tampon 100 has an elongate bullet-shape with a longitudinal direction L and a radial direction R, perpendicular to the longitudinal direction L and an insertion end 106 and a withdrawal end 107, and a middle part 108. Each of the insertion end 106 and the withdrawal end 107 and the middle part 108 occupy approximately one third of the total length of the tampon 101. The insertion end is shown with a rounded tip 117 and a flat withdrawal end surface 120. The tampon length between the tip 117 and the withdrawal end surface 120 may be determined by means of a slide caliper. Tampons commonly have a length in the dry, non-expanded state of from 30 to 70 mm, more common from 40 to 50 mm. The length will commonly vary with the size and design absorption capacity of the tampon. In FIG. 1, the whole surface of the tampon 100 is coated with the lubrication composition 111 in accordance with an embodiment of the present invention. The lubricating composition on the surface of the tampon thus reduces the friction between the tampon and the mucous membrane of the vagina of the user.

The tampon 100 is provided with longitudinally extending grooves or channels in the form of compression lines 108, 109. The compression lines are wave-shaped in FIG. 1 but they may be straight or any other suitable shape.

As described above, the lubricating composition may be also be used on wearable absorbent products to reduce friction between the absorbent product and for example urogenital region of the user and/or other areas of the body of the user.

The lubricating agent may be used on the wearable absorbent product to reduce the friction between the wearable absorbent product and the urogenital region of the user.

Figure 2:
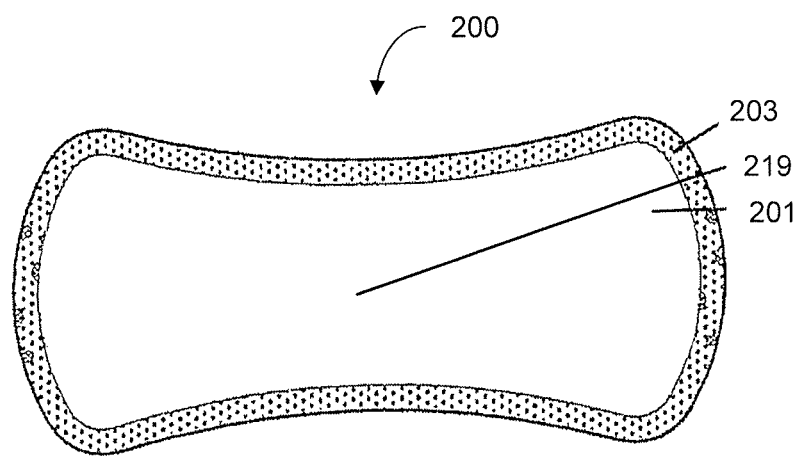
FIGS. 2a-2d show top view of examples of panty liners including the composition according to embodiments of the invention.
Figure 2:
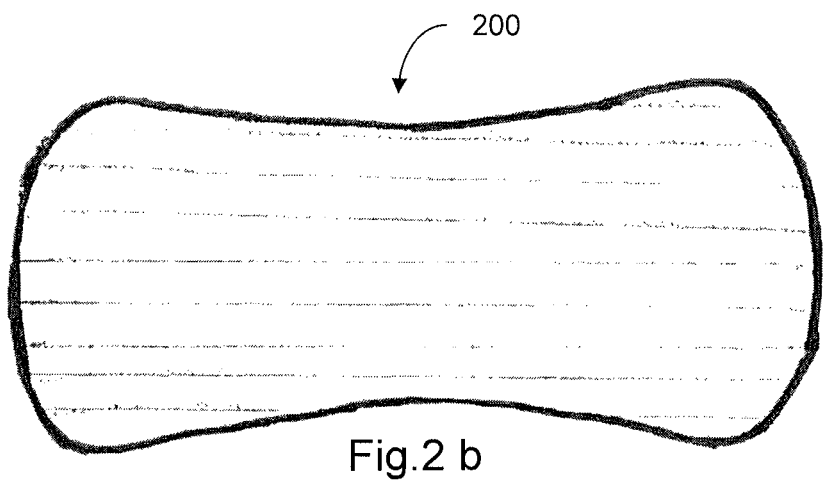
Figure 2:
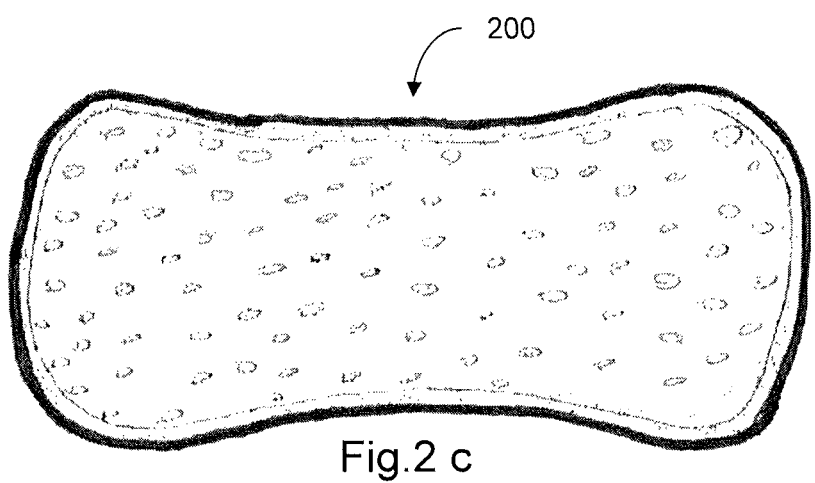
Figure 2:
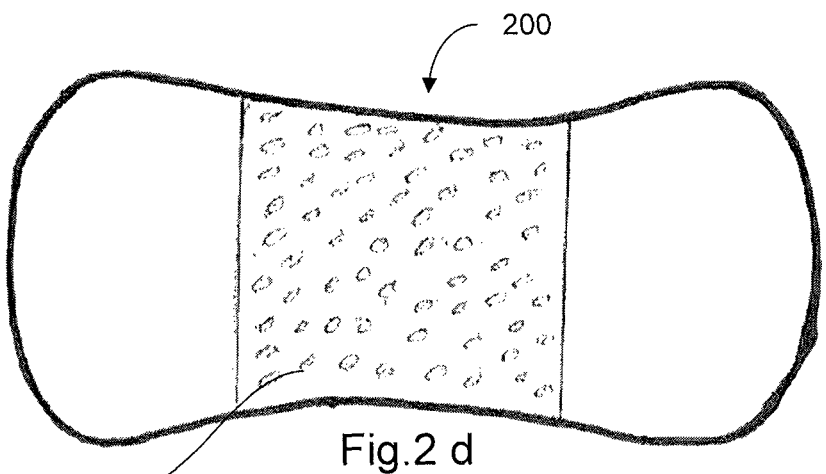

FIGS. 2a-2d schematically show examples of a panty liner 200 in accordance with an embodiment of the present invention. Generally, all the panty liners 200 include a covering layer in the form of a liquid-permeable top sheet 201, as shown in FIG. 2a, that is arranged on the side of the panty liner 200 which during use faces towards the wearer. The panty liner also includes a second covering layer, a back sheet (not shown), which during use faces away from the wearer. Further, the panty liner 200 includes an absorbent core (not shown) arranged between the top sheet 201 and the back sheet. The top sheet and back sheet can be joined together in the reinforcement region 203, as shown in FIG. 2a, for example by means of gluing or ultrasonic welding. Other means for joining together the panty liner may be also used.

As best shown in FIGS. 2a and 2d, the lubricating composition is coated on a crotch region 219 of the panty liner 200. The lubricating composition is applied on the surface of the panty liner 200. The lubricating composition can be positioned in the areas of the wearable absorbent product that come into contact with the urogenital region of the user, i.e. the areas in the crotch region of the wearable absorbent product. In this way, friction may be reduced between the absorbent product and the user while optimal skin care is provided due to the low pH of the composition.

As shown in FIGS. 2c and 2d, the lubricating composition is coated to the surface in a spotted pattern that can be obtained for example by means of printing. In the embodiment shown in FIG. 2b, the lubricating composition is coated to the surface in a striped pattern, which may also be obtained by for example means of printing.

Generally, the printing method may be chosen from any suitable means, e.g. flexographic, gravure or digital printing utilizing e.g. spray application.

Of course, any coating method and the different coating patterns may be used in all kinds of tampons and/or wearable absorbent products.

In another embodiment, only the outer edges on the reinforcement region 203, as illustrated in FIG. 2a, are coated with the lubrication composition to reduce friction between the thighs of the wearer and the panty liner and thus reduce the risk for chafing.

In yet another embodiment, the whole surface of the panty liner 200 is coated with the lubricating composition.

Figure 3:
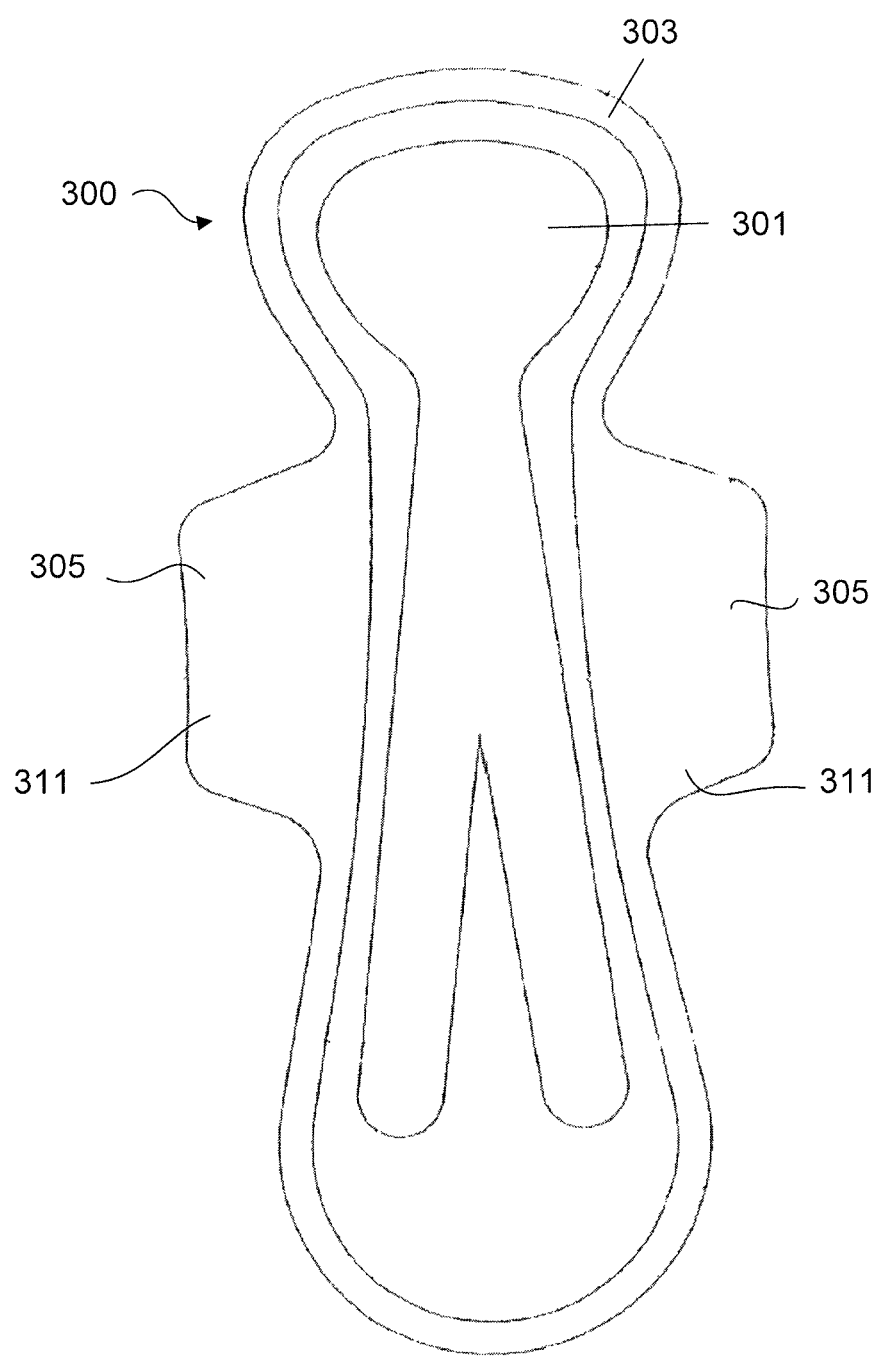
FIG. 3 shows a top view of a sanitary towel including the composition according to an embodiment of the invention.

FIG. 3 shows a sanitary napkin 300 in accordance with an embodiment of the present invention. The sanitary napkin 300 includes a covering layer in the form of a liquid-permeable top sheet 301, which is arranged on the side of the sanitary napkin 300 which during use faces towards the wearer. The sanitary napkin 300 also includes a second covering layer, a back sheet (not shown), which during use faces away from the wearer. The sanitary napkin 300 further includes an absorbent core arranged between the top sheet 301 and the back sheet. The top sheet and back sheet are joined together in the reinforcement region 303 by means of gluing or ultrasonic welding. The sanitary towel includes wings 305 to facilitate the attachment of the sanitary napkin to an undergarment. The sanitary napkin 300 can include the lubricating composition in the crotch region of the napkin, i.e. approximately in the area located between the wings 305 so that the lubricating composition comes into contact with the urogenital region of the user.

Alternatively, the outer edges on the reinforcement region 303 and/or the wings are coated with the lubrication composition 311 to reduce friction between the thighs of the wearer and the panty liner and thus reduce the risk for chafing.

In a similar manner as in connection with the panty liner shown in FIGS. 2a-2d, the lubricating composition may be coated in a specific pattern to the surface of the absorbent product.

Figure 4:
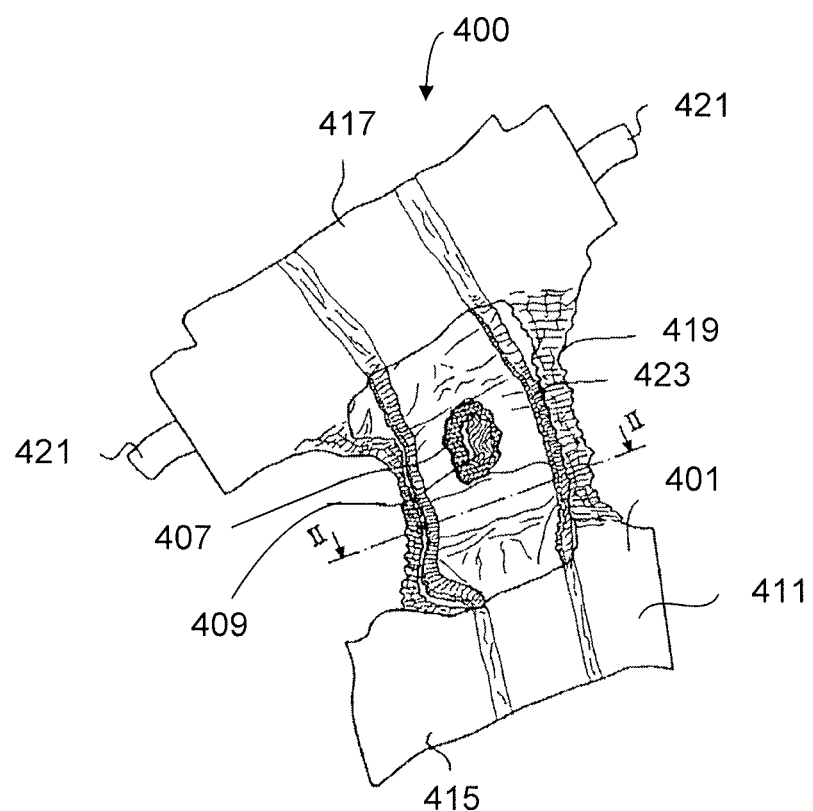
FIG. 4 shows a perspective view of a diaper including the composition according to an embodiment of the invention.

FIG. 4 shows a diaper 400 for an infant or an incontinent adult in accordance with an embodiment of the present invention. The diaper includes a chassis including a liquid permeable top sheet 401, a liquid impermeable back sheet 409 and an absorbent body or core 407 enclosed there between. The top sheet 401 and the back sheet material 409 have a somewhat greater extension in the plane than the absorbent core 407 and extend outside the edges thereof. The layers 401 and 409 are connected to each other within the projecting portions thereof, e.g., by gluing or welding by heat or ultrasonic. The top sheet and/or the back sheet may further be attached to the absorbent core 407 by any method known in the art, such as adhesive, heat-bonding, etc. The absorbent core may also be unattached to the top sheet and/or the back sheet. The diaper 400 includes a front portion 415 intended during use to be worn on the front part of the user's body, a rear portion 417 intended during use to be worn on the rear part of the user's body, and a more narrow crotch region 419 located between the front and rear portions and which is intended to be worn in the crotch region of the user between the legs. The rear portion 417 is provided with a pair of adhesive tape tabs 421 or other type of attachment means such as hook-and-loop type fasteners. The diaper further includes elastic barrier flaps 423 that form leakage barriers and are at their proximal edges secured to the top sheet 401. The diaper 400 may further include an elasticized waist feature in the form of elastic members 411 extending in the transverse direction of the article in the waist portion thereof.

The lubricating composition may be coated on part of the surface facing the wearer, or the composition may be coated for example on the front portion 415 and/or rear portion 417 and/or on the elastic barrier flaps 423, i.e. on the areas where there is a risk for chafing and where friction between the wearer and the diaper needs to be reduced.

Alternatively, the lubricating composition may be coated on the parts of the crotch region 419 that come into contact with the urogenital region of the user. As above, in this way friction may be reduced between the absorbent product and the user while optimal skin care is provided due to the low pH of the composition.

Figure 5:
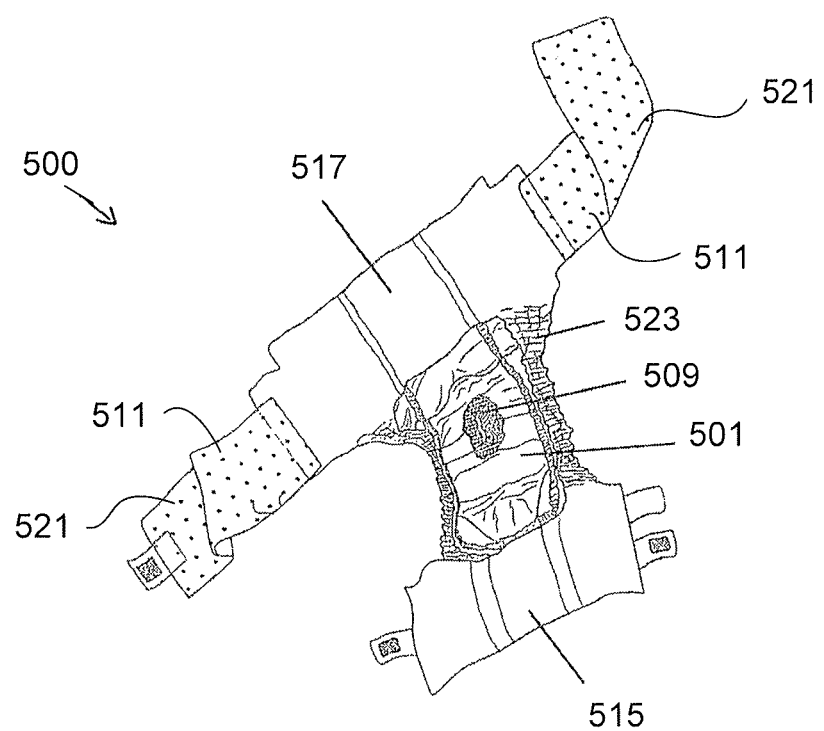
FIG. 5 shows a perspective view of a diaper including a belt including the composition according to an embodiment of the invention.

The diaper 500 shown in FIG. 5, has a similar construction as the diaper in FIG. 4, except that the diaper 500 includes belt portions 511, 521 attached to the rear portion 517 of the diaper 500 and intended to be fastened together around the waist of the wearer. Fastening means on the front part of the diaper are then attached to the outside of the belt to fasten together the diaper to the desired pant-like shape. An example of a belted diaper is shown in WO 01/00129. Similarly as in connection with the diaper shown in FIG. 4, the lubricating composition may be coated on part of the surface facing the wearer, or the composition may be coated for example on the front portion 515 and/or rear portion 517 and/or on the belt portions 511, 521, i.e. on the areas where there is a risk for chafing and where friction between the wearer and the diaper needs to be reduced.

Alternatively, the lubricating composition may be coated on the parts of the crotch region 519 that come into contact with the urogenital region of the user. As above, in this way friction may be reduced between the absorbent product and the user while skin care is provided due to the low pH of the composition.

EXAMPLES

Example 1

This test was performed to show if the lubricating composition including the buffered lactic acid could be used to lower shear forces and hence possibly chafe when for example used on the surfaces of tampons.

Figure 6:
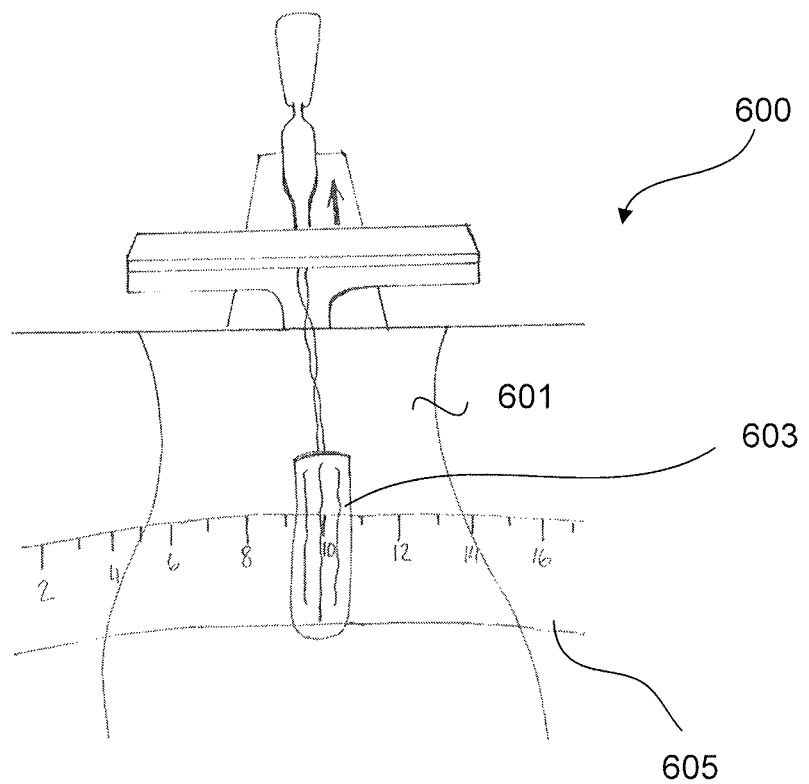
FIG. 6 shows a front view of the arrangement used in example 1 to measure slip-force.
Figure 7:
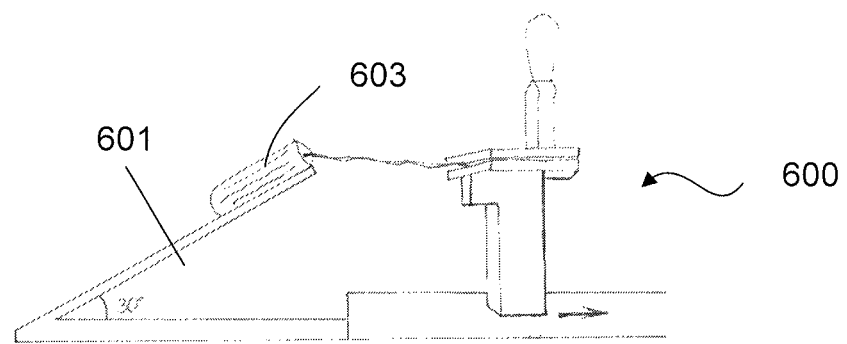
FIG. 7 shows a side view of the arrangement of FIG. 6.

The test was performed using a device illustrated in FIGS. 6 and 7. The device 600 consisted of a flat support surface 601 which was at a 30° angle from horizontal and covered with film, which was prolonged and attached to the support surface. A tampon 603 (Libresse®Normal—new twist wrap) was mounted on this surface and standardized pressed on to this surface by means of a plastic ruler 605. The ruler 605 had a fixed length of 20 cm and was fixed to the flat support surface in the ends. The tampon was always positioned at the centre of the ruler, i.e. at 10 cm.

A tensometer, DIA-STRON MMT 170, measured the force during the pulling of the tampon 603 from its position, pressed to the surface and under the ruler, and out. The Start position was 20 mm, displacement was 50 mm and rate was 150 mm/min. During the process of pulling out the tampon, the force varied. In the Table 1 below, the slip-force (force when tampon starts to move) was registered.

Since there are small variations in size of tampons even within the same package the same tampon was measured both before and after treatment with the lubricating composition including buffered lactic acid. First, the slip-force was measured three times with the untreated tampon and thereafter the lubricating composition was distributed on the surface of the tampon and the slip-force was measured three more times. The lubricating composition was evenly distributed on the lower half of surface of the tampon by means of a tiny brush. The amount of lubricating composition on the tampons was between 0.7-0.8 g. The measured values are also shown in Table 1.

In this test, many different lubricating compositions including buffered lactic acid were tested. The lactic acid was buffered with either potassium lactate or potassium hydroxide. It was buffered to different pH. The lubricating composition was dried to different levels to achieve different water activities. The instrument used to measure water activity was: AquaLab, Model Series 3 TE, Serial# TE8105. It was calibrated using lithium chloride 13.41 M and all measurements were performed in 23 C.

Table 1 below shows the different lubricating compositions and the measured pH, water activity and slip-forces. The slip-force is a mean value from three repetitions.

Figure 8:
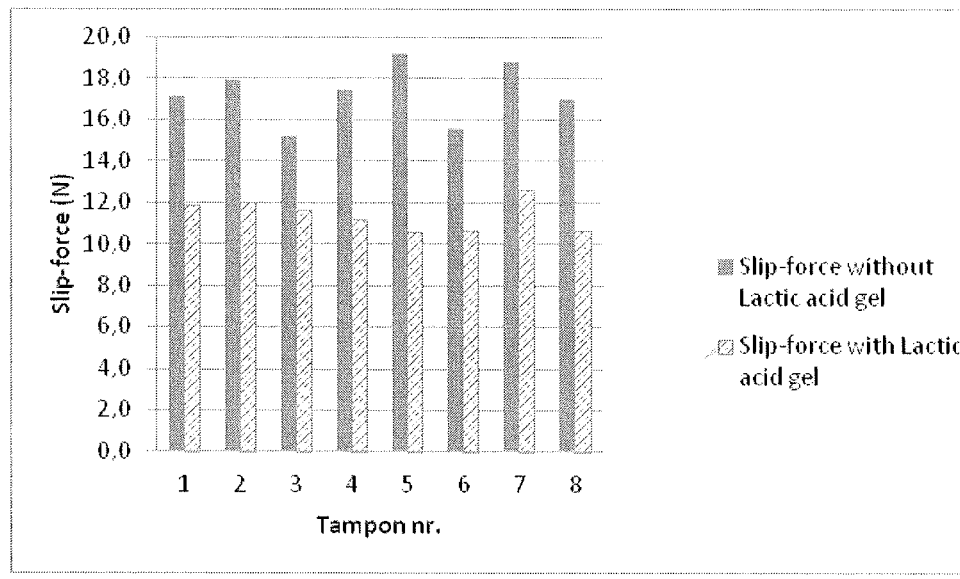
FIG. 8 shows a diagram with the measured slip-force values.

In FIG. 8, the slip force of the tampons is displayed before and after treatment with the lubricating composition.

TABLE 1

The different samples: Tampons with buffered Lactic acid and reference tampon without Lactic acid.

| Tampon number | Salt buffering Lactic acid | Measured pH | Measured water activity (measured at 23° C.) | Measured amount of Lactic acid (g) | Slip-force (N) with Lactic acid | Slip-force (N) Reference without Lactic acid |
|---|---|---|---|---|---|---|
| 1 | Potassium Lactate | 3.7 | 0.42 | 0.79 | 11.85 | 17.14 |
| 2 | Potassium Lactate | 4.6 | 0.41 | 0.70 | 12.03 | 17.93 |
| 3 | Potassium Lactate | 6.2 | 0.29 | 0.79 | 11.62 | 15.20 |
| 4 | Potassium Lactate | 4.0 | 0.80 | 0.80 | 11.18 | 17.43 |
| 5 | Potassium Hydroxide | 3.8 | 0.40 | 0.72 | 10.61 | 19.23 |
| 6 | Potassium Hydroxide | 5.6 | 0.34 | 0.79 | 10.69 | 15.55 |
| 7 | Potassium Hydroxide | 7.1 | 0.23 | 0.73 | 12.66 | 18.81 |
| 8 | Potassium Hydroxide | 4.5 | 0.76 | 0.80 | 10.69 | 17.00 |

Based on the results in the tests it can be concluded that there was a reduced slip-force for all the tampons including the lubricating composition including lactic acid. In all cases, the tampon covered with the composition showed lower slip-force compared to the untreated tampon.

Example 2

This test was performed to investigate if the lubricating composition including buffered lactic acid was able to adjust pH on skin when it was used alone and in a hydrophobic blend with Petrolatum (Snow white P1 from Sonneborn) according to table 2.

0.1 g of the composition was applied on the fore arm skin of a test person as a circular spot of about 2 cm diameter and covered by a plastic film. The composition was kept on the skin for 1 hour. Thereafter the excess of lubricating composition was gently removed with a soft wipe, gently flushed with deionised water and gently dried with a dry piece of paper. After another one minute of rest in air, pH on skin was measured using a pH meter (flat probe VWR™SYMPHONY SB80PI).

The composition used was produced with 15.2 ml of DL-lactic acid solution (85 weight %) which was blended with 46.6 ml potassium lactate solution (50 weight %). This blend was further dried in a dry chamber to a water activity of 0.2. This lubricating composition was further equilibrated in a climate of 25° C. and 50% rH which resulted in a water activity of 0.3. pH on the readymade lubricating composition was measured to be 4.3.

TABLE 2

The different blends

| Sample | Lactate gel (%) | Petrolatum (%) |
|---|---|---|
| 1 | 100 | 0 |
| 2 | 60 | 40 |
| 3 | 10 | 90 |
| 4 | 0 | 100 |

TABLE 3

Measured values of pH

| Sample | Start value Forearm skin | End value Forearm skin |
|---|---|---|
| 1 | 4.9 | 3.5 |
| 2 | 5.3 | 3.5 |
| 3 | 5.3 | 3.6 |
| 4 | 5.4 | 5.1 |

Figure 9:
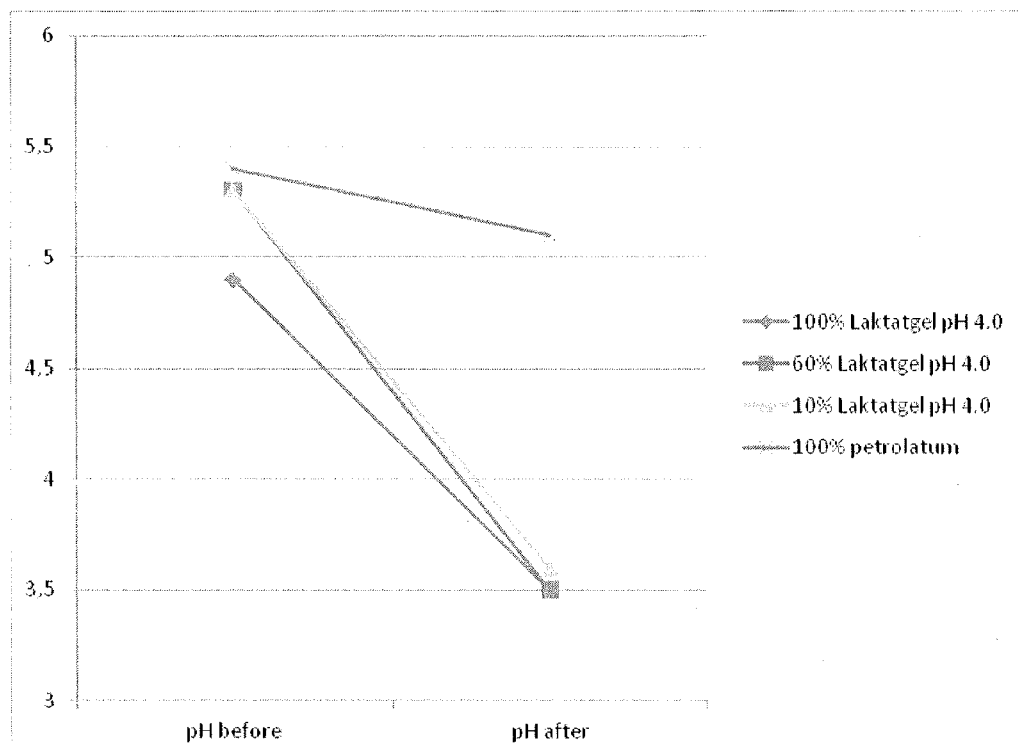
FIG. 9 shows a diagram with the measured pH values.

FIG. 9 figure shows pH on forearm skin—before and after exposure to the samples described in Table 3. As can be seen in FIG. 9 all lubricating composition containing the buffered lactic acid resulted in a pH of about 3.5 after 1 hour of exposure.

Thus it can be concluded that the lubricating composition including buffered lactic acid was able to adjust pH on the fore arm skin—both alone or blended with petrolatum. The same final pH was achieved for all the blends containing the lubricating composition including buffered lactic acid.

The above embodiments are merely illustrative and are in no way intended to limit the present invention.

The invention claimed is:

1. A lubricant composition suitable for contacting mucous membrane or skin, comprising a buffered lactic acid present in an amount from 60 to 100 weight-%, based on the total weight of the lubricant and having a pH within the range of from 3.0 to 6.5, wherein the composition has a water activity of from 0.30 to 0.80, wherein the desired water activity has been obtained by drying.

2. A method for protecting skin and/or mucous membrane against chafing, comprising applying to the skin and/or mucous membrane a layer of the lubricant composition according to claim 1.

3. A method for protecting skin and/or mucous membrane against chafing, comprising applying to at least a portion of a hygiene and/or an absorbent product a layer of the lubricant composition according to claim 1, wherein the composition is brought in contact with the skin of the wearer during use.

4. The lubricant composition according to claim 1, wherein the pH of the composition is within the range of from 3.5 to 5.5.

5. The lubricant composition according to claim 1, wherein the water activity is from 0.30 to 0.60.

6. The lubricant composition according to claim 1, wherein a salt buffering the lactic acid in the composition is an alkali metal salt of lactic acid.

7. The lubricant composition according to claim 6, wherein the alkali metal salt is potassium lactate.

8. The lubricant composition according to claim 1, wherein the composition also comprises an essentially water-free additive.

9. The lubricant composition according to claim 8, wherein the water-free additive is naturally essentially water-free.

10. The lubricant composition according to claim 8, wherein the water-free additive is dried to be essentially water-free.

11. The lubricant composition according to claim 10, the water-free additive is chosen from the group consisting of botanical actives, prebiotic substances, probiotic bacteria, minerals, inorganic additives, salts and vitamins.

12. The lubricant composition according to claim 1, wherein the amount of the buffered lactic acid in the lubricant is about 100 weight-%, based on the total weight of the lubricant.

13. The lubricant composition according to claim 1, wherein the pH of the composition is within the range of from 3.5 to 5.5, wherein the water activity is from 0.34 to 0.80, and wherein a salt buffering the lactic acid in the composition is potassium lactate.

14. An absorbent product comprising the lubricant composition according to claim 1.

15. A lubricant composition suitable for contacting mucous membrane or skin, consisting of a buffered lactic acid present in an amount from 10 to 100 weight-%, based on the total weight of the lubricant and having a pH within the range of from 3.0 to 6.5 and optionally a water-free additive chosen from the group consisting of botanical actives, prebiotic substances, minerals, inorganic additives, salts and vitamins, wherein the composition has a water activity of from 0.30 to 0.80, wherein the desired water activity has been obtained by drying.

16. The lubricant composition according to claim 15, consisting of 0 to 40% by weight water-free additive, based on the total weight of the lubricant and of 60 to 100 wt. % buffered lactic acid.

17. An absorbent product comprising the lubricant composition according to claim 15.

* * * * *